(12) United States Patent
Masson et al.

(10) Patent No.: US 7,195,589 B1
(45) Date of Patent: Mar. 27, 2007

(54) PRESSURE RELIEF PAD FOR USE WITH A CIRCUMFERENTIAL RETRACTOR

(75) Inventors: Marcos V. Masson, Houston, TX (US); Sean H. Lundy, Houston, TX (US); Mark H. Henry, Houston, TX (US)

(73) Assignee: SI-1, Inc., Conroe, TX (US)

( * ) Notice: Subject to any disclaimer, the term of this patent is extended or adjusted under 35 U.S.C. 154(b) by 0 days.

(21) Appl. No.: 10/075,952

(22) Filed: Feb. 15, 2002

(51) Int. Cl.
*A61B 1/32* (2006.01)

(52) U.S. Cl. ........................................ 600/203; 600/208
(58) Field of Classification Search ................ 600/203, 600/201, 208; 604/174, 177, 179, 180; 128/DIG. 26
See application file for complete search history.

(56) References Cited

U.S. PATENT DOCUMENTS

| | | | | | |
|---|---|---|---|---|---|
| 3,696,920 A | * | 10/1972 | Lahay | | |
| 5,474,063 A | * | 12/1995 | Riendeau | ................. | 128/207.9 |
| 5,643,217 A | * | 7/1997 | Dobkin | ....................... | 604/180 |
| 5,681,290 A | * | 10/1997 | Alexander | ................... | 604/180 |
| 5,902,275 A | * | 5/1999 | Dobkin | ....................... | 604/174 |
| 6,458,104 B2 | * | 10/2002 | Gautsche | .................... | 604/179 |

* cited by examiner

*Primary Examiner*—Cary E. O'Connor
(74) *Attorney, Agent, or Firm*—Browning Bushman P.C.

(57) ABSTRACT

A pressure relief pad for use against a body member during orthopaedic surgery including a pad of a resilient material having a first outer surface and a second outer surface. The first outer surface has a slot extending longitudinally thereacross. The slot has a width suitable for receiving surgical tubing therein. The second outer surface has a contour suitable for placement against the body member. The surgical tubing will extend through the slot while the pad is interposed between the surgical tubing and the body member. Retractor paddles can be attached to the opposite ends of the surgical tubing for the purposes of retracting the incision during surgery.

11 Claims, 2 Drawing Sheets

PRESSURE RELIEF PAD FOR USE WITH A CIRCUMFERENTIAL RETRACTOR

BACKGROUND OF THE INVENTION

1. Field of the Invention

The present invention relates to surgical retractor apparatus. More particularly, the present invention relates to pressure relief pads used to prevent nerve damage and to improve circulation during surgery. Additionally, the present invention relates to pressure relief pads that can be used with circumferential retractors during surgery.

2. Description of Related Art

Surgical "retraction" is the drawing back of body tissue. When the operation involves making an incision, the incision itself often must be retracted. During surgery, internal organs, bones and tissues are intermittently retracted through the opening created in the retracted incision.

In certain surgeries, an assistant's fingers are used as retractor paddles. However, greater technical ease is available through the use of various mechanical retractor systems. Mechanical retractor systems can be divided into two major groups: externally mounted "fixed" to the operating table and self-retaining retractors.

The mechanical systems attached to the operating table present the same type of physical obstruction to the surgeon's movement as presented by the assistant's body, arms and hands since the externally fixed retractor systems of a vertical column, supporting arm(s) or ring and retractor paddles attached thereto. The retractor paddles, support arms or ring and vertical column in these apparatus are adjustable in multiple planes and axes of motion; however, these retractor paddles are not all independently adjustable in the vertical plane. Movement of a support arm or ring of these apparatus necessitates movement of all retractor paddles attached thereto.

Ideally, mechanical retractors, both externally mounted and self retaining, need to provide for internal organ and tissue retraction, be quickly and easily assembled, positioned and repositioned in all planes and axes of motion, present as little obstruction to the surgeon's movement as possible, protect the sterile field, diminish the risk of tissue trauma and yet be stable enough to function adequately while reducing the need for assistance.

Self-retaining retractors that have attempted to provide for internal organ and tissue retraction through the open incision have failed to permit quick, independent, easy and safe adjustment of internal organ and tissue retractor paddles in all planes and axes of motion, and in effect the prior art is either ineffectual or unsafe, or both since these paddles are not easily adjustable in the vertical plane and such internal organ and tissue retractor paddles must traverse over (or through) internal tissue before reaching the desired location along the retractor handle and/or frame. The retractor paddle depth is not highly variable and the retractor paddles' location on the retractor frame is limited.

In the past, various patents have issued relating to such retractors. For example, U.S. Pat. No. 5,520,610, issued on May 28, 1996 to Giglio, describes a self-retaining retractor. This retractor includes flexible, resilient retractor paddles which can be placed into the incision. A rigid frame is provided which includes two interlocking halves laid longitudinally over the incision. The incision retractor paddles are manually clipped to each frame half, and then the frame halves are opened to the desired extent. The incision retractor paddles and the frame provide the apparatus with stability for retraction of internal organs and tissues through the open incision by the addition of mounting jigs containing adjustment posts onto mounting means which radiate outwardly from the frame.

U.S. Pat. No. 5,931,777, issued on Aug. 3, 1999 to G. A. Sava, teaches a tissue retractor with particular use in spinal surgery. This tissue retractor includes a pair of pivotally linked arms, each with a blade mounted thereto by a ball-and-socket joint so as to allow free movement of the blades relative of the arms. The blades have an anchoring end to anchor to the bone. The retractor is operable by placing the blades in a wound opening, securing the anchoring ends to a portion of the bone in a position apart from each other, and operating the retractor to cause the blades to separate and to retract tissues surrounding the wound opening by outward pivoting of the blades relative to the position of the anchoring ends.

U.S. Pat. No. 6,074,343, issued on Jun. 13, 2000 to Nathanson et al., describes a surgical tissue retractor comprised of a plurality of retractor blades that can be operated simultaneously. Right and left retractor blades are mounted on an actuator mechanism that spreads or expands the blades as a rotatable primary actuator knob is rotated. A third retractable arm is mounted for simultaneous operation with the right and left retractor blade or independent operation through a secondary rotatable actuator knob that extends or retracts a threaded shaft attached to the center retractor blade.

U.S. Pat. No. 6,090,043, issued on Jul. 18, 2000 to Austin et al., describes a tissue retractor including a hook, a handle and an elastomeric band. The hook has a tissue-engaging portion and is retained by the handle such that the tissue engaging portion extends from a first end of the handle. The handle end of the band is retained by a second end of the handle. The back has a longitudinal body and at least one hub disposed about the body.

One of the present inventors developed a circumferential retractor apparatus which is presently the subject of U.S. patent application Ser. No. 09/916,819, filed on Jul. 30, 2001. This application describes a circumferential retractor apparatus having a first retractor paddle having a grasping surface and a body portion supporting the grasping surface, a second retractor paddle having a grasping surface and a body portion supporting the grasping surface, and an elastic member having one end received by the first retractor paddle and an opposite end received by the second retractor paddle. Each of the paddles has a hole formed therein of a size suitable for allowing the elastic member to pass therethrough. A slot is formed in the body portion so as to open to the hole. The slot is of a tapered configuration so as to have a wide end opening to the hole and a narrow end away from the hole. The grasping surface includes a plurality of fingers extending outwardly of the body portion. Each of the plurality of fingers are arranged in parallel spaced relationship to each other. The elastic member is a length of surgical tubing. During surgery, the grasping surface of the first retractor paddle engages one side of the incision while the grasping surface of the second retractor paddle engages the opposite side of the incision. The tension in the surgical tubing will maintain the incision in an open condition. The surgical tubing will extend around the body member in a tensioned condition.

Since the surgical tubing has a relatively small diameter, the pressure applied by the surface of the surgical tubing to the body member has relatively great force in pounds per square inch. As such, a need has developed so as to remedy the problem of pressure applied against the body member and to reduce the possibility of nerve damage or impaired circulation during surgery.

It is an object of the present invention to provide a pressure relief device which can be used with elastic members associated with circumferential retractors.

It is another object of the present invention to provide a pressure relief device which can eliminate or significantly reduce any pressures applied by surgical tubing to the body member subjected to surgery.

It is a further object of the present invention to provide a pressure relief device which is adaptable to a wide variety of types of surgery and adaptable to different shapes of body members.

It is still a further object of the present invention to provide a pressure relief device which is easy to manufacture, relatively inexpensive and easy to use.

These and other objects and advantages of the present invention will become apparent from a reading of the attached specification and appended claims.

BRIEF SUMMARY OF THE INVENTION

The present invention is a pressure relief pad for use against a body member during orthopaedic surgery comprising a body of a resilient material having a first outer surface and a second outer surface. The first outer surface has a slot extending longitudinally thereacross. The slot has a width suitable for receiving surgical tubing therein. The second outer surface has a contour suitable for placement against the body member.

This body has a first end surface and a second end surface tapering inwardly from the second outer surface toward the first outer surface. The first outer surface has an inverted V-shaped configuration. The slot is positioned at an apex of this inverted V-shaped configuration. The slot has one end opening at the first end surface and an opposite end opening at the second end surface. The slot is a tubular slot having a generally circular cross-section with an opening extending longitudinally therealong. An adhesive can be applied onto the second outer surface so that the body can be adhesively affixed to the body member.

In an alternative form of the present invention, a plurality of slots extend across the first outer surface. This plurality of slots includes multiple slots extending in generally parallel relationship to each other along the first outer surface, a first angled slot extending angularly across the multiple slots, and a second angled slot extending across the multiple slots. The first and second angled slots have a generally X-shaped configuration.

The present invention is also a circumferential retractor apparatus which comprises a first retractor paddle having an interior grasping surface and a body portion supporting the grasping surface, a second retractor paddle having an interior grasping surface and a body portion supporting this grasping surface, an elastic member having one end received by the first retractor paddle and an opposite end received by the second retractor paddle, and a pad having a slot formed therein. The slot in the pad receives the elastic member between the ends of the elastic member. The slot extends across the first outer surface of the pad.

When used in surgery, the body member will have an incision formed therein. The grasping surface of the first retractor paddle engages one side of the incision. The grasping surface of the second retractor paddle engages an opposite side of the incision. The elastic member extends around the body member away from this incision. The pad is interposed between the elastic member and the body member. The elastic member is of surgical tubing. The slot is a tubular slot having an opening extending longitudinally therealong. This opening has a width less than a diameter of the surgical tubing. The slot has one end opening at the first end surface of the pad and an opposite end opening at the second end surface of the pad. The surgical tubing extends outwardly of the slot at these ends. The second outer surface of the pad has a contour generally matching a contour of the body member. The second outer surface of the pad is adhesively affixed to the body member.

DETAILED DESCRIPTION OF THE INVENTION

Figure 1:
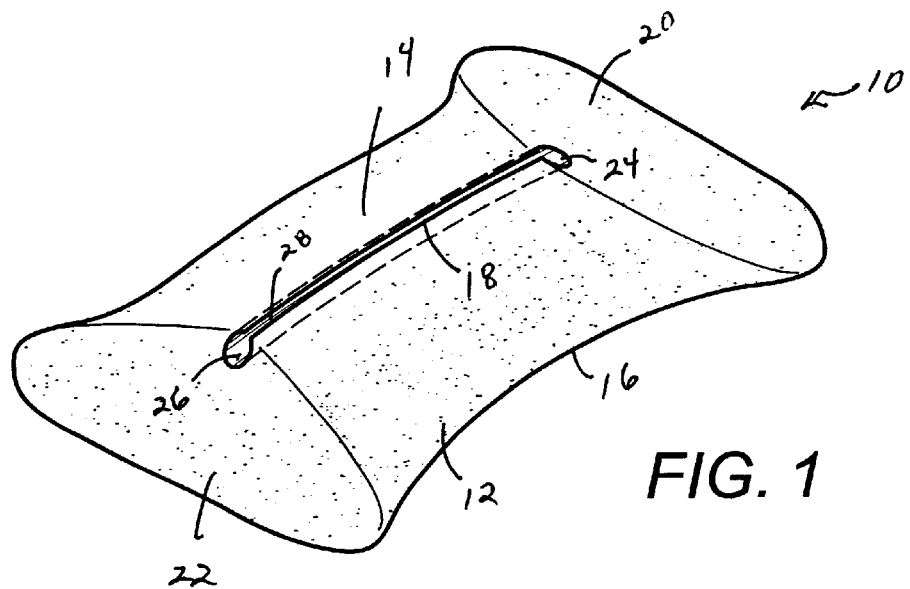
FIG. 1 is a perspective view of the pressure relief device in accordance with the preferred embodiment of the present invention.

Referring to FIG. 1, there is shown the pressure relief pad 10 in accordance with the preferred embodiment of the present invention. The pressure relief pad 10 is suitable for use against a body member during surgery. The pressure relief pad 10 includes a body 12 formed of a resilient material, such as a polymeric foam. The body 12 includes a first outer surface 14 and a second outer surface 16. The first outer surface 14 has a slot 18 extending longitudinally thereacross. This slot 18 is a tubular slot having a diameter suitable for receiving surgical tubing therein. The second outer surface 16 has a contour suitable for placement against the body member.

As can be seen in FIG. 1, the body 12 includes a first end surface 20 and a second end surface 22. The first end surface 20 tapers inwardly from the second outer surface 16 toward the first outer surface 14. Similarly, the second end surface 22 tapers inwardly from the second outer surface 16 toward the first outer surface 14. It can be seen that the end 24 of the slot 18 opens at the top of the first end surface 20. The opposite end 26 of the slot 18 opens at the top of the second end surface 22. The slot 18 has an opening 28 extending longitudinally thereacross and along the first outer surface 14. Opening 28 is of a width which is less than the diameter of the surgical tubing. As a result of the opening 28, the surgical tubing can be placed into the slot 18 and be firmly retained therein.

Figure 2:
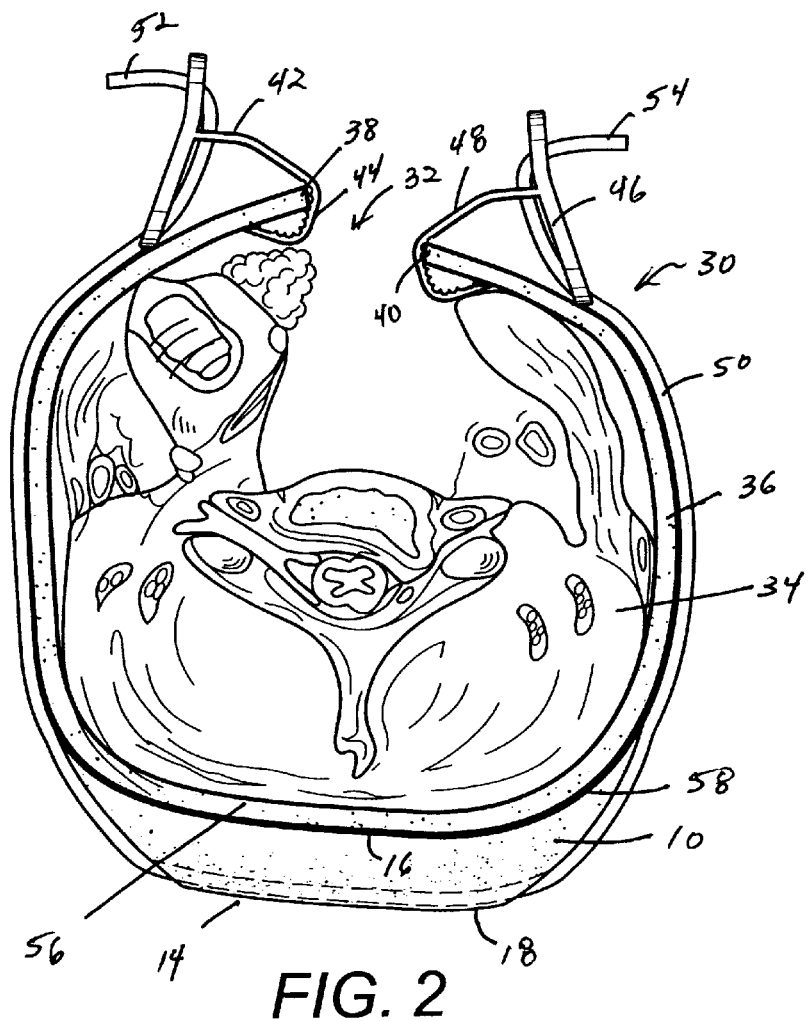
FIG. 2 is an illustration showing the use of the pressure relief pad during surgery on a body member.

FIG. 2 shows how the pad 10 can be used in association with a circumferential retractor apparatus 30 during a surgical procedure. In FIG. 2, it can be seen that an incision 32 has been formed in a limb 34. When the incision 32 is made, the skin 36 will have one edge 38 and an opposite edge 40 which are separated. After an incision is made, a first retractor paddle 42 is placed over the edge 38 such that the grasping surface 44 of the first retractor paddle 42 engages the edge 38 of skin 36. Similarly, a second retractor paddle 46 is placed over the edge 40 such that the grasping surface 48 of the second retractor paddle 46 engages the edge 40 of skin 36.

As can be seen in FIG. 2, the surgical tubing 50 has one end 52 engaged with the first retractor paddle 42. Similarly, the surgical tubing 50 has a second end 54 engaged with the second retractor paddle 46. In particular, the tubing 50 will extend through a slot formed at the bottom of the retractor paddle 42, through a hole formed in the grasping portion and be received within a slot formed at the top of the retractor paddle 42. The opposite end 54 is received in a similar manner by the second retractor paddle 46. The surgeon can then apply suitable tension to the surgical tubing 50 so as to properly retract the edges 40 and 44 of the incision 32 in a desired manner. The surgical tubing 50 will extend around the limb 34 away from the incision 32.

Importantly, it can be seen that the pad 10 is positioned on the opposite side 56 of the limb 34 away from the incision 32. The second outer surface 16 is shown as having a contour which generally matches a contour of the limb 34 around the skin 36. An adhesive 58 can be applied to the second outer surface 16 of the pad 10 so as to securely adhere the pad 10 to the opposite side 56 of the limb 34.

The tubing 50 is shown as being received within the slot 18 on the first outer surface 14 of the pad 10. The pressure caused by the tensioned tubing 50 will further cause the pad 18 to be retained against the skin 36 of limb 34.

Importantly, in FIG. 2, it can be seen that the pressures of the tubing 50 are applied against a much wider surface area relative to the limb 34. By distributing the forces of the tubing 50 over a wider surface area, the pounds per square inch of force against the skin are minimized.

Figure 3:
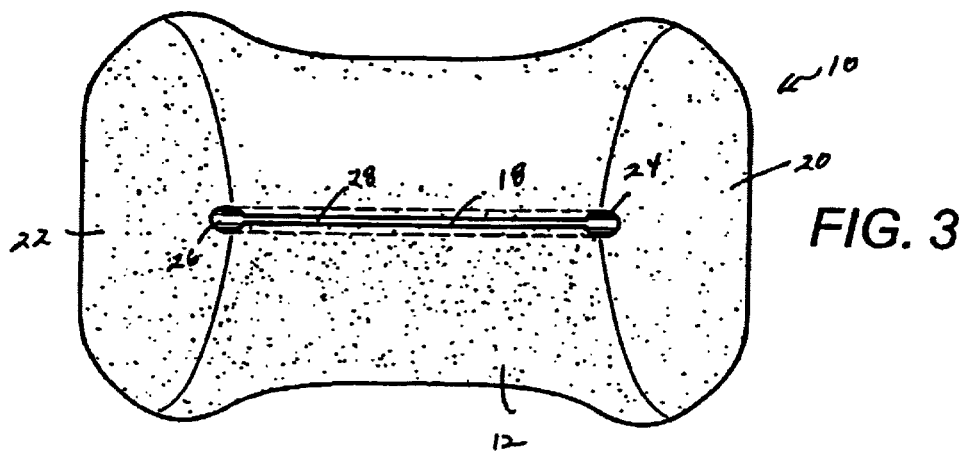
FIG. 3 is a plan view of the pressure relief pad of the present invention.

FIG. 3 shows a plan view of the body 12 of pressure relief pad 10. The slot 18 has opening 28 extending longitudinally therealong. The opening 20 has a width which is less than the diameter of the tubular slot 18. End 26 of the slot 18 will open at the second end surface 22. Similarly, end 24 of the slot 18 will open at end surface 20 of the body 12. When the surgical tubing is placed within the slot 18, the opposite ends of the surgical tubing will emerge outwardly of the ends 24 and 26 of the slot 18.

Figure 4:
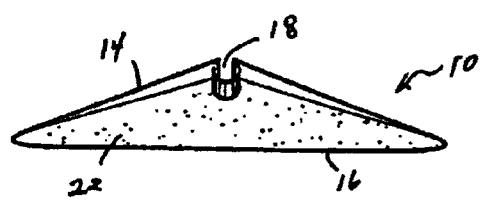
FIG. 4 is an end view of the pressure relief pad of the present invention.

In FIG. 4, the second end surface 22 of the pressure relief pad 10 is particularly illustrated. As can be seen, the first outer surface 14 has a generally inverted V-shaped configuration. Slot 18 will extend along the apex of the inverted V-shaped configuration of the first outer surface 14. The second outer surface 16 will be generally flat at the end surface 22.

Figure 5:
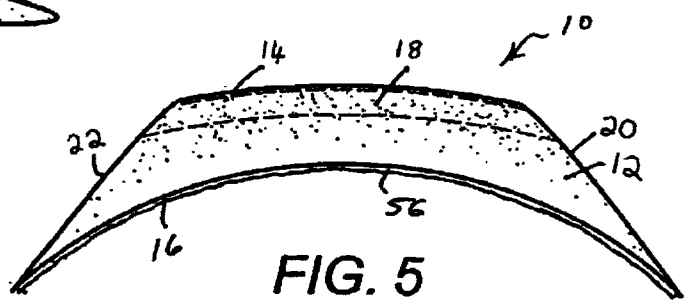
FIG. 5 is a side elevational view of the pressure relief pad of the present invention.

FIG. 5 shows an isolated side view of the pressure relief pad 10 of the present invention. Importantly, in FIG. 5, it can be seen that the second end surface 16 has a contour which can be shaped so as to generally match the contour of the body member. A suitable adhesive 58 can be applied to the second outer surface 16 so as to allow the second outer surface 16 to be adhered to the body member during the surgery. Since the body 12 of the pad 10 is formed of a resilient material, such as a polymeric foam, the second outer surface 16 can be further manipulated so as to properly conform to the contour of the limb. In FIG. 5, it can be seen that the second end surface 22 tapers inwardly from the outer periphery of the second outer surface 16 toward the outer periphery of the first outer surface 14. Similarly, the first end surface 20 will taper inwardly from the outer periphery of the second outer surface 16 toward the outer periphery of the first outer surface 14. The slot 18 is illustrated in broken line fashion as extending through the adhesive pad 12 so as to open at the respective end surfaces 20 and 22.

Figure 6:
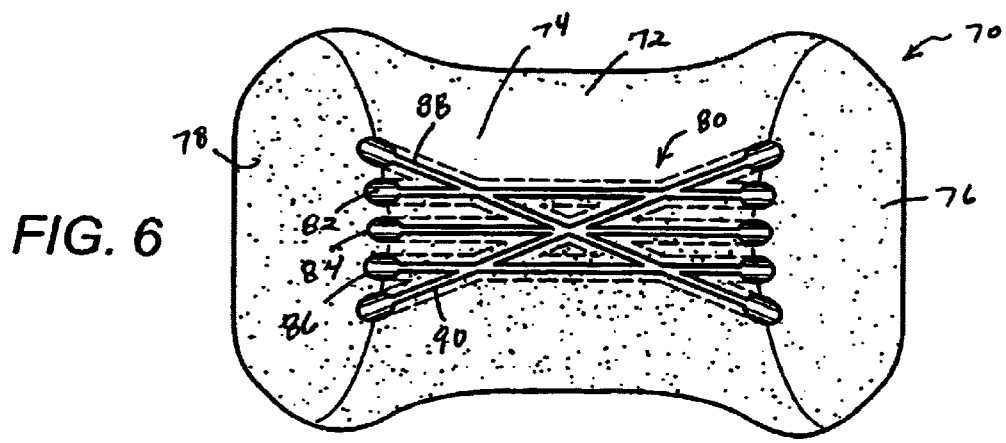
FIG. 6 is a plan view showing an alternative embodiment of the pressure relief pad of the present invention.

FIG. 6 shows an alternative embodiment of the pressure relief pad 70 of the present invention. The pressure relief pad 70 has a body 72 of a similar configuration to that of body 12 shown in FIG. 1. Body 72 has a first outer surface 74 and a second outer surface (not illustrated). End surfaces 76 and 78 will extend from the second outer surface inwardly toward the first outer surface 74. Importantly, in FIG. 6, it can be seen that in place of the singular slot 18 of the previous embodiment, this alternative embodiment of the pressure relief pad of the present invention has a plurality of slots 80 extending across the first outer surface 74 of the body 72.

The plurality of slots 80 include multiple slots 82, 84 and 86 extending longitudinally across the first outer surface 74 in generally parallel relationship to each other. Each of these slots 82, 84 and 86 has one end opening at the first end surface 76 and an opposite end opening at the second end surface 78. A first angled slot 88 extends angularly across the first outer surface 74 and across the multiple slots 82, 84 and 86. A second angled slot 90 also extends angularly across the multiple slots 82, 84 and 86 on the first outer surface 74 of the body 72. The first angled slot 88 is in a X-shaped configuration with the second angled slot 90. Once again, the angled slots 88 and 90 have respective ends opening at the first end surface 76 and the end surface 78. Each of the slots 82, 84, 86, 88 and 90 has a structure similar to that of the slot 18 of the previous embodiment so as to properly retain surgical tubing therein. The arrangement of the various slots 82, 84, 86, 88 and 90, as shown in FIG. 6, allow the surgical tubing to be adjusted in various ways depending on the surgical procedure employed or the angular positioning of the particular limb. Under certain circumstances, the incision may be angularly offset from the longitudinal axis of the limb. As a result, the pad 70 can be properly utilized so as to minimize pressure applied by the surgical tubing to the limb while achieving a proper orientation of the surgical tubing with respect to the retractor paddles.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

We claim:

1. A pressure relief pad for use against a body member during surgery comprising:
 a body of a resilient material having a first outer surface and a second outer surface, said first outer surface having a plurality of slots extending thereacross, each of plurality of slots having a width suitable for receiving surgical tubing therein, said second outer surface having a contour suitable for placement against the body member, said plurality of slots comprising:
 multiple slots extending across said first outer surface in generally parallel relation to each other;
 a first angled slot extending angularly across said multiple slots; and
 a second angled slot extending angularly across said multiple slots, said first and second angled slots having a generally X-shaped configuration.

2. The pad of claim 1, said body having a first end surface and a second end surface, said first and second end surfaces tapering inwardly from said second outer surface toward said first outer surface.

3. The pad of claim 2, each of said plurality of slots having one end opening at said first end surface and an opposite end opening at said second end surface.

4. The pad of claim 1, said first outer surface having an inverted V-shaped configuration, at least one of said plurality of slots being positioned at an apex of said inverted V-shaped configuration.

5. The pad of claim 1, each of said plurality of slots being a tubular slot having a generally circular cross-section, the slot having an outer opening suitable for allowing the surgical tubing to be placed thereinto.

6. The pad of claim 1, further comprising:
an adhesive means applied to said second outer surface of said body for adhesively affixing said body to the body member.

7. The pad of claim 1, said resilient material being o a polymeric foam.

8. A circumferential retractor apparatus comprising:
a first retractor paddle having an interior grasping surface, said first retractor paddle having a body portion supporting said grasping surface;
a second retractor paddle having an interior grasping surface, said second retractor paddle having a body portion supporting said grasping surface;
an elastic member having one end received by said first retractor paddle and an opposite end received by said second retractor paddle; and
a pad having a slot formed therein, said slot receiving said elastic member between said ends of said elastic member.

9. The apparatus of claim 8, said pad having a first outer surface, a second outer surface, a first end surface extending between said first and second outer surfaces, and a second end surface extending between said first and second outer surfaces, said slot extending longitudinally across said first outer surface.

10. The apparatus of claim 9, said elastic member being surgical tubing, said slot being a tubular slot having an opening extending longitudinally therealong, said opening having a width less than a diameter of said surgical tubing, said slot having one end opening at said first end surface and an opposite end opening at said second end surface, said surgical tubing extending outwardly of said slot at said ends thereof.

11. The apparatus of claim 9, said second outer surface of said pad having a contour generally matching a contour of said body member.

* * * * *